US008487640B2

(12) United States Patent
Bradley

(10) Patent No.: US 8,487,640 B2
(45) Date of Patent: Jul. 16, 2013

(54) INTERNAL NODE RESISTANCE TESTING FOR A TIRE

(75) Inventor: Calvin Rhett Bradley, Greenville, SC (US)

(73) Assignees: Compagnie Generale des Establissements Michelin (FR); Michelin Recherche et Technique S.A. (CH)

( * ) Notice: Subject to any disclaimer, the term of this patent is extended or adjusted under 35 U.S.C. 154(b) by 350 days.

(21) Appl. No.: 13/070,575

(22) Filed: Mar. 24, 2011

(65) Prior Publication Data

US 2012/0169357 A1 Jul. 5, 2012

Related U.S. Application Data

(60) Provisional application No. 61/428,390, filed on Dec. 30, 2010.

(51) Int. Cl.
*G01R 27/08* (2006.01)

(52) U.S. Cl.
USPC .......... 324/691; 324/525; 73/146.5; 73/146.8

(58) Field of Classification Search
USPC ........................ 324/525, 691; 73/146.5, 146.8
See application file for complete search history.

(56) References Cited

U.S. PATENT DOCUMENTS

| 2,503,992 | A | * | 4/1950 | Becker .......................... 324/552 |
| 4,516,068 | A | | 5/1985 | Hawkins, Jr. | |
| 4,520,307 | A | | 5/1985 | Weiss | |
| 6,600,326 | B2 | | 7/2003 | Weiss | |
| 6,802,212 | B2 | | 10/2004 | Farn | |
| 6,837,102 | B2 | | 1/2005 | Weiss | |
| 6,907,777 | B2 | | 6/2005 | Weiss | |
| 2009/0072842 | A1 | | 3/2009 | Murakami | |
| 2009/0078034 | A1 | | 3/2009 | Range | |

FOREIGN PATENT DOCUMENTS

| GB | 688055 A | 2/1953 |
| JP | 2000009771 A | 1/2000 |
| JP | 2000238505 A | 9/2000 |
| JP | 2003054228 A | 2/2003 |
| JP | 2008247068 A | 10/2008 |

* cited by examiner

*Primary Examiner* — Vincent Q Nguyen
(74) *Attorney, Agent, or Firm* — Frank J. Campigotto

(57) ABSTRACT

Methods for measuring the electrical resistance of a tire including establishing contact between a tread face portion of the omega section and a grounded conductive surface and establishing contact between a mounting portion of the omega section and a mounting rim. An embodiment further includes measuring electrical resistance between each of two or more internal nodes of the omega section and the grounded conductive surface, wherein the two or more internal nodes are each a metal component cured in the tire and measuring electrical resistance between each of the two or more internal nodes of the omega section and the mounting rim and measuring electrical resistance between each of the two or more internal nodes of the omega section. A method may further include identifying a least conductive portion of the omega section as being the portion having the highest measured electrical resistance.

10 Claims, 3 Drawing Sheets

INTERNAL NODE RESISTANCE TESTING FOR A TIRE

PRIORITY CLAIM

This application claims the benefit of previously filed U.S. Provisional Patent Application entitled "Internal Node Resistance Testing For A Tire," assigned U.S. Ser. No. 61/428,390, filed Dec. 30, 2010, and which is incorporated by reference in its entirety for all purposes.

BACKGROUND OF THE INVENTION

1. Field of the Invention

This invention relates generally methods for measuring electrical resistance and more particularly, to methods for measuring electrical resistance in tires across parts of tires.

2. Description of the Related Art

Moving vehicles may experience a buildup of static electricity of relatively high voltage unless a grounding path is provided to dissipate the charge. Such charge buildup is undesirable for a number of reasons including, for example, having an adverse impact on the vehicle's electronic circuitry, e.g., its radio reception and having an adverse impact on an occupant of the vehicle when the occupant experiences an electrical shock upon providing a path to ground for the built-up charge, typically upon the occupant entering or exiting the vehicle.

To prevent the buildup of the static electricity in the vehicle, the charge may be dissipated by providing a continuous ground to earth from the vehicle. Previously, particularly for larger vehicles, a ground was provided by dragging along a chain or other electrical conductor connected to the frame of the vehicle. As the vehicle moved, a charge was conducted to the ground along the chain.

Preferably, tires can provide the path to ground for dissipating the electrical charge. However, not all materials that might be used in tire construction are necessarily electrically conductive. Rubber compositions that are electrically conductive are typically constructed from compounds having significant proportions of conductive carbon black. Conversely, rubber compositions that are relatively nonconductive tend to have significantly larger amounts of silica relative to carbon black since, increasing the relative proportion of silica relative to carbon black typically decreases conductivity.

It is desirable, therefore, for tire manufactures to provide tires that dissipate any static electricity to ground to prevent the buildup of charge in the vehicle. Determining whether a tire has an adequate design for such dissipation is desirable.

SUMMARY OF THE INVENTION

Particular embodiments of the present invention include methods for measuring the resistance of an omega section of a tire. An embodiment includes establishing contact between a tread face portion of the omega section and a grounded conductive surface and establishing contact between a mounting portion of the omega section and a mounting rim. An embodiment further includes measuring electrical resistance between each of two or more internal nodes of the omega section and the grounded conductive surface, wherein the two or more internal nodes are each a metal component cured in the tire and measuring electrical resistance between each of the two or more internal nodes of the omega section and the mounting rim and measuring electrical resistance between each of the two or more internal nodes of the omega section. A method may further include identifying a least conductive portion of the omega section as being the portion having the highest measured electrical resistance.

A particular embodiment of the present invention includes a method for measuring the electrical resistance of a section of a tire. An embodiment includes providing the section cut from the tire, the section including a proximal end, a distal end and at least one metal component that is cured into the tire section, wherein the proximal end is nearest a bead portion of the tire and the distal end is nearest a tread portion of the tire. An embodiment further includes establishing contact between the distal end and a first conductive surface, establishing contact between the proximal end and a second conductive surface and providing a ground from one of the first conductive surface and the second conductive surface. An embodiment may further include measuring electrical resistance between the metal component and the first conductive surface, measuring electrical resistance between the metal component and the second conductive surface and measuring electrical resistance between the first conductive metal surface and the second conductive surface. Further included may be identifying a least conductive portion of the section of tire as being the portion having the highest measured electrical resistance.

The foregoing and other objects, features and advantages of the invention will be apparent from the following more detailed descriptions of particular embodiments of the invention, as illustrated in the accompanying drawing wherein like reference numbers represent like parts of the invention.

DETAILED DESCRIPTION OF PARTICULAR EMBODIMENTS

Particular embodiments of the present invention include methods for determining the electrical resistance through portions of a tire. When designing, a tire to ensure that the tire will adequately discharge the static electricity buildup from a vehicle, it is recognized that the tire must have adequate conductivity to allow the charge to dissipate from the wheel-tire assembly to the road. Electrical resistance of a tire-inversely measures the ability of the tire to dissipate static charge from the vehicle.

One method of measuring the electrical resistance of a tire is the ASTM F1971 test method entitled *Standard Test Method for Electrical Resistance of Tires under Load on the Test Bench*. Under this method, the electrical resistance is measured between the wheel upon which an inflated tire is mounted and a flat conducting surface in contact with the tire. While such a method does adequately measure the electrical resistance across a tire, it does not provide a means, for those tires that were deemed not adequately conductive under the test, for determining what section of the tire was not as conductive as it was supposedly designed to be.

There are currently two different types of methods utilized for characterizing electrical properties of a tire; one type that measures the properties of the materials in the tire and one type that measures the electrical resistance of the whole tire, such as the ASTM F1971 test method. A tire is typically designed with both materials and architecture that provide an adequate electrical path through the tire to dissipate the electrical charge buildup in the vehicle.

Such design criteria take into account two fundamental measurements of electrical conductivity—resistance and resistivity. Resistance is a measure of how strongly an object opposes the passage of a steady electric current. Resistivity is a measure of how strongly a material opposes the flow of an electric current. Resistivity is therefore independent of the geometry of an object and is merely a measure of a property of the material. Resistance, however, is affected by the geometry of the object and therefore, the architecture of a tire influences the resistance of the tire. It is therefore a tire design consideration to ensure that materials of suitably low resistivity are placed in juxtaposition to provide the electrical path to ground through the tire.

Figure 1:
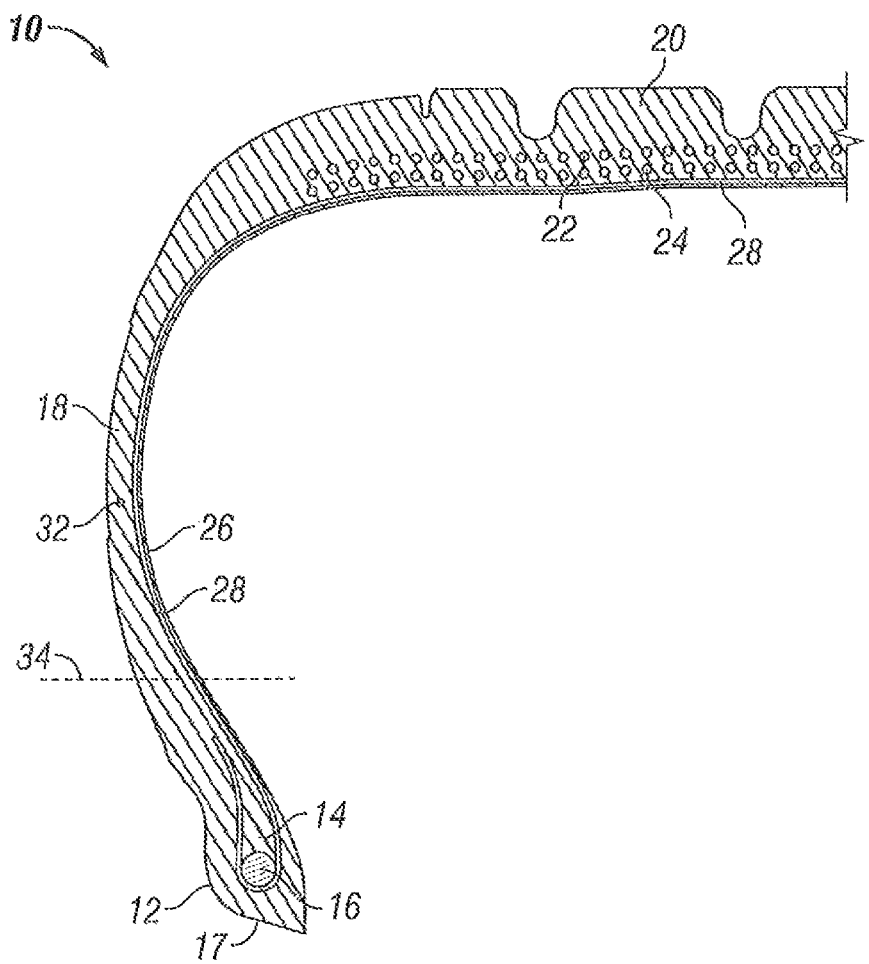
FIG. 1 is a cross sectional view of one-half of a exemplary pneumatic tire.

With reference to FIG. 1, a cross sectional view of one-half of an exemplary pneumatic tire is shown. The tire 10 includes a tread 20 component that makes contact with the road to provide traction. The sidewall 18 component protects the tire 10 from side scuffing and provides support for the tread 20. The belt package 22, 24 includes layers of textile or wire, typically steel wire, lying under the tread 20 to stiffen the casing and provide improved tire performance. The bead 16 is typically formed from nonextensible steel wire loops that anchor the cords 28 and hold the tire onto a wheel assembly (not shown) so that the tire 10 will not slip on the wheel rim. The area around the beads 16 include components that protect the bead and/or stabilize the area, such components including the toe guard 17, the chafer 12 and the apex 14. The plies or cords 28 extend from bead to bead 16, typically wrapped around and turned up from the bead, and provide the primary reinforcing material in the tire casing. The inner liner 26 is the innermost layer of the tire and provides a barrier to minimize the leakage of inflation gases through the tire 10.

Figure 2:
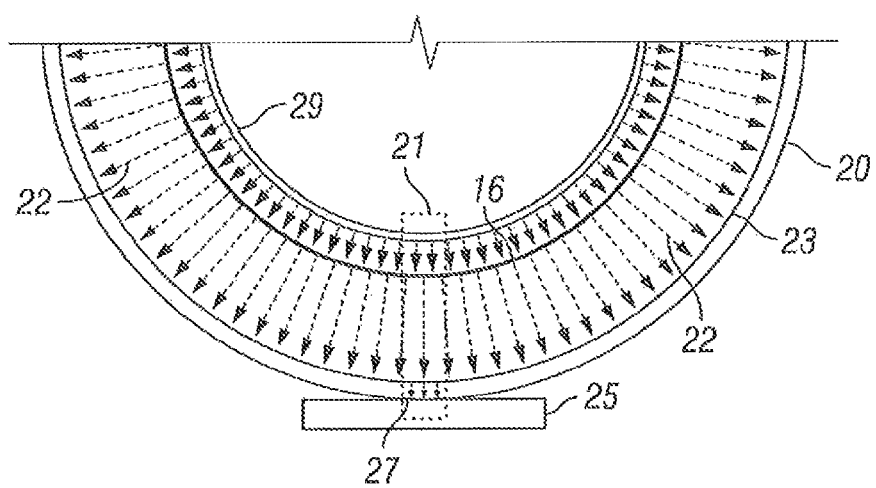
FIG. 2 is a schematic of a simplified discharge path in a tire for an electrical charge to ground.

FIG. 2 is a schematic of a simplified discharge path in a tire for an electrical charge to ground. The static electricity charge generated by a vehicle flows to ground from the wheel 29 on which the tire is mounted to the road 25. The contact between the road 25 and the tire 10 is made at the contact patch 27, where the tire tread 20 meets the road 25. Those components made up generally of metal have hear constant potential around the circumference of the tire—those metal components being the wheel 29, the bead 16 and the belt package 23. The charge 22 travels more slowly through the rubber sections of the tire, such as the sidewall 18, the chafer 12, the apex 14 to the metal components and then more quickly through the metal components. Very little of the charge, if any, flows through the inner liner 26, typically made of material having relatively high resistivity and having no direct contact with any of the metal components of the tire. All the charge 22, however, passes to ground through the contact patch 27 since that is the only contact between the road 25 and the tire 10.

The section between the wheel 29 and the tread 20 above the contact patch 27 is an omega section 21, named such because it has a shape similar to the Greek letter omega. Indeed it is the same shape as the section of tire 80 illustrated in FIG. 4. Typically a section of tire cut from the tire between the beads and the tread is called an omega cut.

Particular embodiments of the present invention provide a solution for troubleshooting electrical resistance issues when a tire fails a whole tire testing method such as the ASTM F1971 test method. When the whole tire resistance testing method provides an unexpectedly high resistance measurement that cannot be easily resolved from materials testing and/or an initial examination of the tire architecture, a test method for pinpointing the part of the tire having high resistance is desirable.

Previously, to try to pinpoint low conductivity areas in a tire, a method, included inserting pins into an omega cut of a tire and measuring the resistance between the pins to determine the zone of high resistance. While this method was highly flexible and allowed for testing between any two points on the tire, the repeatability of the testing was problematic, with depth of the pins and the distance between the pins being highly influential on the test result. Also, the contact between the pins and the rubber was not particularly good since the pins were not cured into the rubber but were merely inserted into the cured tire.

To overcome these issues, particular embodiments of the present invention test electrical resistance between two or more internal nodes of a tire, wherein the internal nodes are metal components cured into the tire. Natural internal nodes include the belt package of the tire and the bead of the tire, each of which are predominantly metal components and are cured into the tire. Since these natural internal nodes are cured into the tire and extend throughout the entire circumference of the tire, the components have a large surface contact with the tire rubber and have good adherence to the rubber, thereby providing nodes for measuring resistance between parts of the tire.

In particular embodiments, additional metal components may be cured into a tire for testing purposes. Such additional metal components may include, for example, one or more wires and/or bands of metal cured into the tire, thereby forming an internal node having a high surface contact area with the rubber of the tire and, because the metal components are cured into the tire, good adherence to the tire rubber. Such metal components may, for example, be cured into the tire in a radial direction, a circumferential direction or in any suitable arrangement useful for determining a high resistance section in a tire. For example, in FIG. 1 a wire 32 is cured into the tire sidewall to provide an internal node for testing.

The internal nodes formed by metal components cured into the tire provide locations that divide the tire into sections for testing and for determining each section's conductivity. Two other natural locations or nodes that may be useful as test nodes include the road or the surface upon which the tread of the tire is in contact and the wheel or wheel section-upon which the tire is mounted or in contact. Resistance testing may be performed to determine the resistance between each of these nodes to rank the conductivity of the different sections of the tire from the highest conductivity section to the lowest conductivity section of those sections tested.

Figure 3:
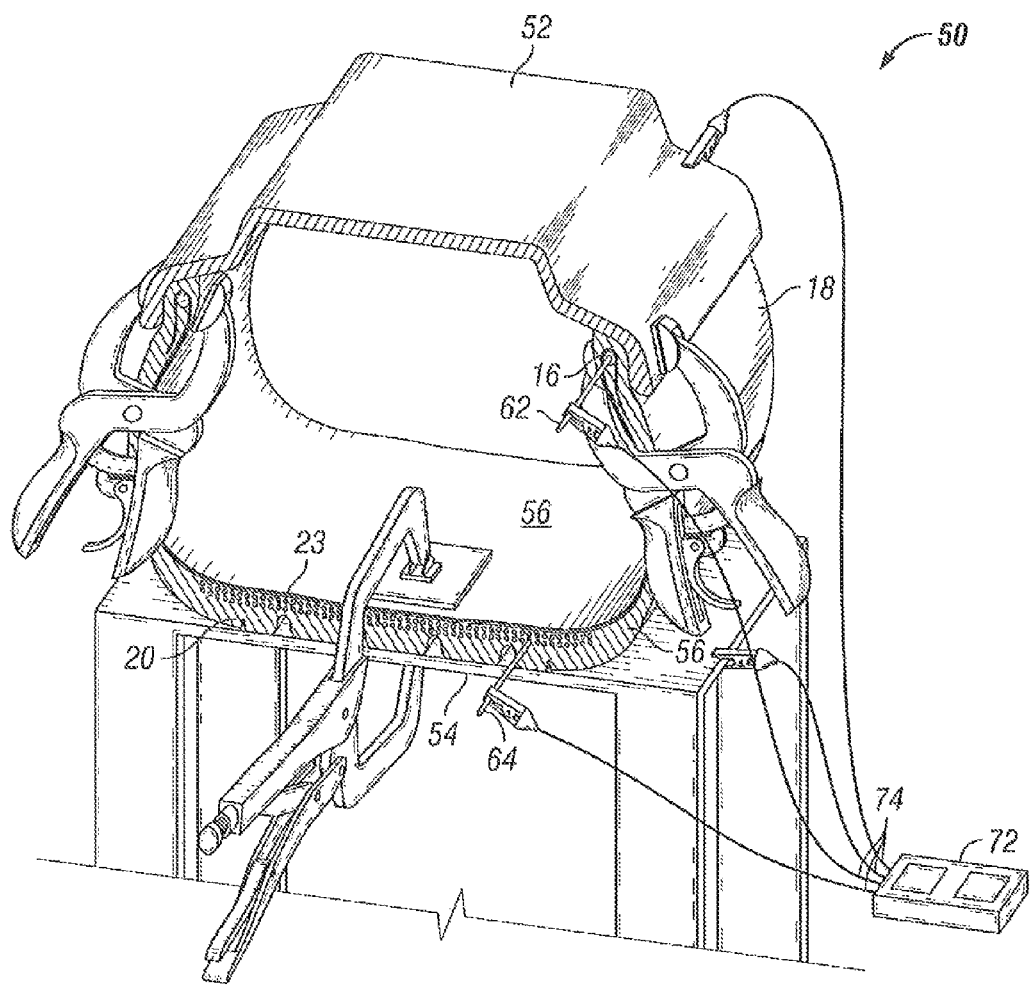
FIG. 3 is a perspective view of an omega cut of a tire on a test stand in accordance with an exemplary embodiment of the present invention.

FIG. 3 is a perspective view of an omega cut of a tire on a test stand in accordance with an exemplary embodiment of the present invention. In FIG. 3, a testing apparatus 50 is illustrated having an omega cut 56 (about 50 mm wide) of a tire clamped to a grounded metal plate 54. The omega cut 56 is also clamped to a wheel section 52 to simulate a tire mounted on a wheel. A pin 64 is inserted into the belt package 23 and another pin 62 is inserted into the bead 16. The pins 62, 64 are shown in contact with the metal components. A resistance meter 72 is attached with leads 74 running to the wheel section 52, the two pins 62, 64 and the grounded metal plate 54 upon which the tread 20 is clamped. The resistance meter may then be used to measure between any two of the nodes, which include the wheel section 52, the bead 16, the grounded metal plate 54 and the belt package 23. Although not shown, in particular embodiments an insulating film may be placed between the omega cut 56 and the metal clamps holding it in place.

Figure 4:
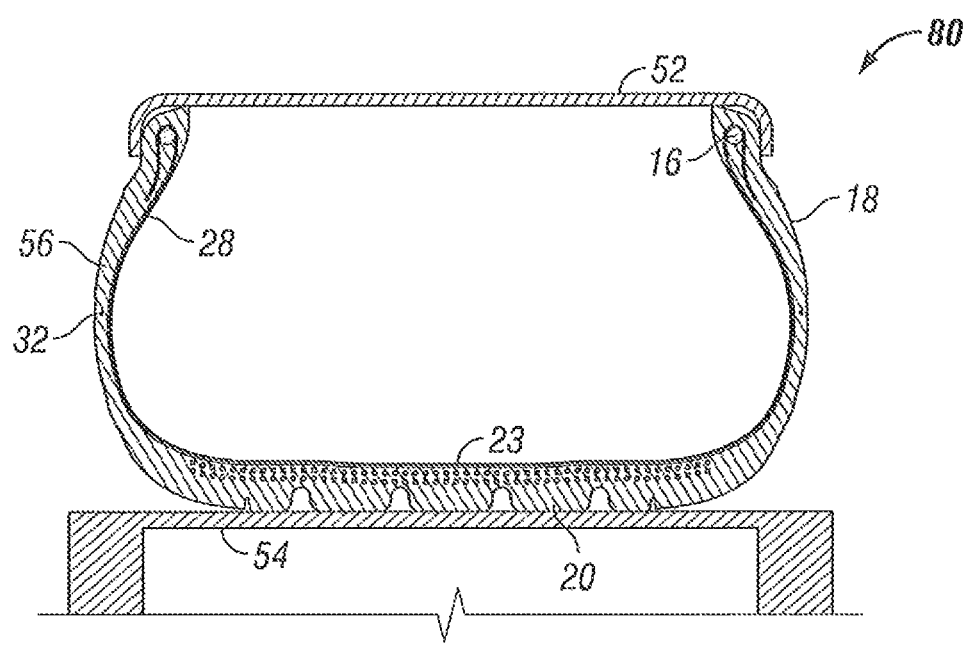
FIG. 4 is a schematic of the internal and external test nodes of an exemplary omega cut on a tire in accordance with a particular embodiment of the present invention.

FIG. 4 is a schematic of the internal and external test nodes of an exemplary omega cut on a tire in accordance with a particular embodiment of the present invention. In the simplified schematic of FIG. 4, the four test nodes are illustrated. Measurements may be taken, for example, with a resistance meter between any two of the test nodes. The four test nodes are the metal plate 54, the belt package 23, the bead 16, the wheel section 52 and the wire 32 cured into the tire to create a test node.

In a particular embodiment, a method for measuring the electrical resistance of an omega section of a tire includes establishing contact between the tread face portion of the omega section and a grounded conductive surface such as a metal plate. Conductive materials or devices, as used herein, are those having a conductivity of at least, $1 \times 10^6$ Siemens per meter. For example, stainless steels may have a conductivity of about $1.3 \times 10^6$ Siemens per meter while aluminum has a conductivity of about $35 \times 10^6$ Siemens per meter and carbon steel a conductivity of about $5.9 \times 10^6$ Siemens per meter.

If the omega section is an omega cut from a tire, the omega cut may be clamped to the grounded conductive surface so that the tread is pressed against the surface to assure good contact between the tread face and the grounded conductive surface. If the omega section is the portion of a tire pressed against the grounded conductive surface, a force may be imposed, for example, to the top of the tire or by loading an axle to press the tread face of the omega section against the conductive surface. If an omega cut is used, particular embodiments include an omega cut that is between 10 mm and 100 mm wide or alternatively, between 30 mm and 70 mm or between 40 mm and 60 mm wide. However, the invention is not limited to these exemplary dimensions and other embodiments may have varying sizes of omega cuts.

In particular embodiments, contact is also established between the mounting portion of the omega section and the mounting rim of a wheel upon which the tire is mounted. If the omega section is an omega cut from a tire, then in particular embodiments the mounting portion of the tire may be contacted with the mounting rim, such as by clamping or otherwise engaging the mounting portion with the mounting rim. The mounting rim may be, for example, a section of rim that has been cut from a wheel or a simulated mounting rim shaped to provide contact between the mounting portion of the omega cut and the mounting rim. The mounting portion of the omega section is the portion of the bead area of the tire that is designed to contact and engage the wheel upon which the tire is mounted. In particular embodiments, the mounting rim is formed from a conductive material. In particular embodiments, the mounting rim is formed from aluminum and/or carbon steel.

The grounded conductive surface and the mounting rim are two external nodes for testing the conductivity of the omega section. Measuring the electrical resistance between the conductive metal plate and the mounting rim provides a measurement of the electrical resistance between the mounting rim and the grounded conductive plate and an indication of the conductance of the omega section and/or tire.

Particular embodiments may further include measuring the electrical resistance between each of two or more internal nodes of the omega section and the grounded conductive surface. This measured electrical resistance determines the electrical resistance between each of the internal nodes and the grounded conductive surface. The internal nodes are components of the tire that comprise metal and that are cured into the tire.

The electrical resistance may be measured between the two or more internal nodes and the mounting rim to determine the electrical resistance between each of the internal nodes and the mounting rim. Additionally the electrical resistance may be measured between each of the two or more internal nodes to determine the electrical resistance between each of the internal nodes.

The internal nodes, being components comprising metal and cured into the tire, may be, for example, the bead of the tire and the belt package. Other wires or cables or metal components that are cured into the tire may act as internal nodes for the purpose of better determining a problem section of a tire, i.e., a section of the tire having low electrical conductivity. In particular embodiments, such metal components may be cured into a test tire solely for the purpose of providing internal nodes for resistance testing and without regard to the tire performance since the usefulness for such a tire is limited to electrical conductance testing.

If a whole tire is being tested instead of an omega cut, then the internal nodes are not exposed since they are internal to the tire. In particular embodiments of a whole tire being tested, the internal nodes are accessed by inserting a pin into the tire to contact the metal component within the tire. The internal nodes may be accessed by cutting away some of the rubber on the outside of the tire to expose the internal nodes.

Each of the measured electrical resistances between the different nodes may be recorded and may be ranked to identify the least conductive portion of the omega section and/or tire as being the portion having the highest measured electrical resistance. In this manner, the section of the tires may be ranked from the one having the highest electrical resistance to the lowest electrical resistance.

The invention is not limited to evaluating only omega sections of a tire for conductivity and may include evaluating other sections of a tire. For example, in FIG. 1 an exemplary cutting line 34 is shown where the tire section may be cut to provide a section of tire halving a distal end nearest the tread 20 portion of the tire, a proximal end closest to the bead 16 portion of the tire and having at least one metal component cured; into the tire section.

For example, a tire cut along the cutting line 34 would provide two different tire sections. The tire section above the cutting line 34 would include the tread 20 as the distal end of the tire section and the cut end of the sidewall 18 as the proximal end of the tire section. The tire section below the cutting line 34 would include the cut end of the sidewall 18 as the distal end and the bead 16 end of the section as the distal end.

If the tire section is that section below the cut line 34, then the first end would be at the bead area and the second end would be the end at the cut line. The bead would be a metal component cured into the tire section. If the tire section is that section above the cut line 34, then the first end would be the end at the cut line 34 and the second end would be the tread 20.

A particular embodiment includes a method for pleasuring the electrical resistance of a section of a tire. Such method may include providing the section cut from the tire, the section including a proximal end, a distal end and at least one/ metal component that is cured into the tire section. The method further includes establishing contact between the distal end and a first conductive surface and establishing contact between the proximal end and a second conductive surface. If the distal end is the tread face, then in a particular embodiment, the first conductive surface may be grounded. In particular embodiments, the first conductive surface or the second conductive surface is grounded.

If the end is a tread face or the bead section, then the tread face of bead section may be contacted with the conductive surfaces as described previously, e.g., by pressing the tread face against the conductive surface or clamping the bead section to a mounting rim portion.

However, if the end is the cut end, such as the cut sidewall described above, then contact between the end and the conductive surface may be made by clamping or otherwise pressing the end against the conductive surface. In a particular embodiment, to enhance the contact and conductivity between the end and the conductive surface, a metal paint or other coating that enhances conductivity may be applied to the end. Such conductive paints, including silver-based paints, are well known and readily available.

Particular embodiments further include measuring the electrical resistance between the metal component and the conductive surfaces at each end of the section. If there is more than one metal component-cured into the rubber in the section cut, then the resistance between each of the metal components will also provide an indication of the conductance between the metal components.

Each of the measured electrical resistances between the different nodes may be recorded and may be ranked to identify the least conductive portion of the cut section as being the portion having the highest measured electrical resistance. In this manner, the sections of the cut section may be ranked from the one having the highest electrical resistance to the lowest electrical resistance.

The terms "comprising," "including," and "having," as used in the claims and specification herein, shall be considered as indicating an open group that may include other elements not specified. The term "consisting essentially of," as used in the claims and specification herein, shall be considered as indicating a partially open group that may include other elements not specified, so long as those other elements do not materially alter the basic and novel characteristics of the claimed invention. The terms "a," "an," and the singular forms of words shall be taken to include the plural form of the same words, such that the terms mean that one or more of something is provided. The terms "at least one" and "one or more" are used interchangeably. The term "one" or "single" shall be used to indicate that one and only one of something is intended. Similarly, other specific integer values, such as "two," are used when a specific number of things is intended. The terms "preferably," "preferred," "prefer," "optionally," "may," and similar terms are used to indicate that an item, condition or step being referred to is an optional (not required) feature of the invention. Ranges that are described as being "between a and b" are inclusive of the values for "a" and "b."

It should be understood from the foregoing description that various modifications and changes may be made to the embodiments of the present invention without departing from its true spirit. The foregoing description is provided for the purpose of illustration only and should not be construed in a limiting sense. Only the language of the following claims should limit the scope of this invention.

What is claimed is:

1. A method for measuring electrical resistance of an omega section of a tire, the method comprising:
    establishing contact between a tread face portion of the omega section and a grounded conductive surface;
    establishing contact between a mounting portion of the omega section and a mounting rim;
    measuring electrical resistance between each of two or more internal nodes of the omega section and the grounded conductive surface, wherein the two or more internal nodes are each a metal component cured in the tire;
    measuring electrical resistance between each of the two or more internal nodes of the omega section and the mounting rim;
    measuring electrical resistance between each of the two or more internal nodes of the omega section; and
    identifying a least conductive portion of the omega section as being the portion having the highest measured electrical resistance.

2. The method of claim 1, wherein the two or more internal nodes comprise a bead and a belt package.

3. The method of claim 2, wherein the two or more internal nodes further comprise a test wire cured into the tire.

4. The method of claim 1, wherein the metal component comprises one of more metal wires.

5. The method of claim 1, further comprising:
    clamping the omega section to the grounded conductive surface; and
    pressing the tread face portion against the grounded conductive surface.

6. The method of claim 1, wherein the omega section has been cut from the tire.

7. A method for measuring electrical resistance of a section of a tire, the method comprising:
    providing the section cut from the tire, the section including a proximal end, a distal end and at least one metal component that is cured into the tire section, wherein the proximal end is nearest a bead portion of the tire and the distal end is nearest a tread portion of the tire;
    establishing contact between the distal end and a first conductive surface;
    establishing contact between the proximal end and a second conductive surface;
    providing a ground from one of the first conductive surface and the second conductive surface;
    measuring electrical resistance between the metal component and the first conductive surface;
    measuring electrical resistance between the metal component and the second conductive surface;
    measuring electrical resistance between the first conductive metal surface and the second conductive surface; and
    identifying a least conductive portion of the section of tire as being the portion having the highest measured electrical resistance.

8. The method of claim 7, further comprising:
    coating at least one of the distal end and proximal end with a coating that improves the conductivity between the coated end and the conductive surface.

9. The method of claim 7, wherein the at least one internal node is selected from a bead, a belt package, a wire, a cable or combinations thereof.

10. The method of claim 9, wherein the tire section includes two or more metal components cured into the tire section, further comprising:
    measuring electrical resistance between each of the two or more metal components.

* * * * *